United States Patent [19]

Rooney et al.

[11] 4,025,625

[45] May 24, 1977

[54] IMIDAZOTHIAZINES

[75] Inventors: Clarence S. Rooney, Beaconsfield; Joshua Rokach, Laval, both of Canada; Edward J. Cragoe, Jr., Lansdale, Pa.

[73] Assignee: Merck & Co., Inc., Rahway, N.J.

[22] Filed: June 15, 1976

[21] Appl. No.: 696,259

[52] U.S. Cl. .......................... 424/246; 260/243 R
[51] Int. Cl.² ............ C07D 279/08; C07D 279/14; A61K 31/54
[58] Field of Search ............... 260/243 R; 424/246

[56] References Cited

UNITED STATES PATENTS

| | | | |
|---|---|---|---|
| 3,749,781 | 7/1973 | Mandel | 424/251 |
| 3,821,381 | 6/1974 | Mandel | 424/251 |
| 3,821,409 | 6/1974 | Mandel | 424/332 |
| 3,824,311 | 7/1974 | Mandel | 424/267 |
| 3,824,315 | 7/1974 | Mandel | 424/251 |
| 3,973,017 | 8/1976 | Anderson | 260/243 R |

*Primary Examiner*—John M. Ford
*Attorney, Agent, or Firm*—William H. Nicholson; Harry E. Westlake, Jr.

[57] ABSTRACT

Dihydro- and tetrahydro-imidazothiazines are inhibitors of indoleamine-N-methyl transferase in vivo.

9 Claims, No Drawings

IMIDAZOTHIAZINES

BACKGROUND OF THE INVENTION

This invention is concerned with dihydro- and tetrahydro-imidazothiazines and derivatives thereof which by virtue of their ability to inhibit indoleamine-N-methyl transferase are useful in the treatment of certain mental aberrations in man, such as schizophrenia.

This invention also relates to processes for the preparation of the compounds of this invention; to pharmaceutical compositions comprising the compounds; and to a method of treating mental aberrations, such as schizophrenia, comprising the administration of the compounds and compositions thereof. The novel compounds may be depicted by the generic structure:

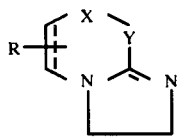

wherein X—Y is —CH$_2$—S— or —S—CH$_2$—.

N,N-dimethylindoleamines such as dimethylserotonin and dimethyltryptamine are psychotomimetic agents and are believed to be produced in excessive amounts by individuals with certain mental aberrations, most commonly classified as schizophrenia. Indoleamine-N-methyl transferase is an enzyme which catalyzes the methylation steps in the biosynthesis of these compounds. Accordingly, it is believed by those skilled in the art that inhibitors of this enzyme will be of therapeutic value in management of the body chemistry of patients having mental aberrations such as schizophrenia and thus result in alleviating some of the symptoms of the disease. Thus it is an object of the present invention to provide the above-described compounds and their pharmaceutically acceptable acid addition salts; to provide processes for the preparation of such compounds; pharmaceutical compositions comprising such compounds; and to provide methods of treatment comprising administering such compounds and compositions, when indicated for the treatment/management of mental aberrations such as schizophrenia.

DETAILED DESCRIPTION OF THE INVENTION

The novel compounds of this invention have structural formula I:

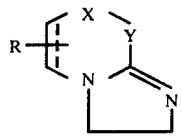

or pharmaceutically acceptable salt thereof, wherein
the dotted line represents saturation or unsaturation,
X-Y represents —CH$_2$—S— or —S—CH$_2$—; and
R represents C$_{1-2}$ alkyl, especially methyl;
with the proviso that when X-Y represents —S—CH$_2$—, the dotted line represents unsaturation.

One embodiment of the novel compounds of this invention is that with structural formula:

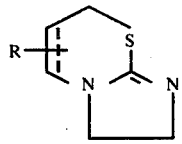

or pharmaceutically acceptable salt thereof.

The pharmaceutically acceptable salts of this invention are acid addition salts prepared from mineral or organic acids commonly employed in the pharmaceutical art, such as hydrobromic, hydrochloric, fumaric, ethane disulfonic, or the like.

The compound, 2,3,5,6-tetrahydro-8H-imidazo[2,1-c][1,4] thiazine, excluded from the novel compounds is included in the disclosure of U.S. Pat. application, Ser. No. 593,412, filed July 7, 1975, now U.S. Pat. No. 3,973,017.

In the novel method of treatment of this invention the route of administration can be oral, rectal, intravenous, intramuscular, or intraperitoneal. Doses of 0.10 to 100 mg./kg./day and preferably of 1 to 10 mg./kg./day of active ingredient are generally adequate, and it is preferred that it be administered in divided doses given two to four times daily.

It is to be noted that the precise unit dosage form and dosage level depend upon the case history of the individual being treated and, consequently, are left to the discretion of a skilled therapist.

Pharmaceutical compositions comprising a compound useful in the novel method of treatment as active ingredients may be in any art recognized form suitable for oral use, such as tablets, troches, lozenges, aqueous or oil suspensions, dispersible powders, or granules, emulsions, hard or soft capsules, syrups, or elixirs. For intravenous and intramuscular and intraperitoneal use the pharmaceutical compositions may be in any art recognized form of a sterile injectable preparation such as a sterile aqueous oleaginous solution or suspension. The amount of active ingredient incorporated in a unit dosage of the above described pharmaceutical compositions may be from 1 mg. to 500 mg.

The compounds of this invention are prepared by the following processes:

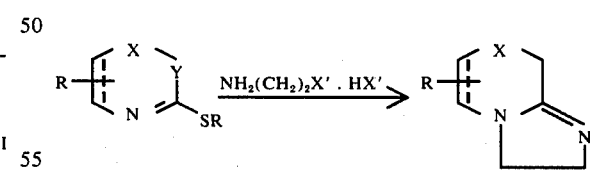

wherein —X—Y—, and R have the meanings previously assigned, and X' is chloro or bromo.

The process comprises heating at 50°–100° C. for 3–10 hours, an approximately equimolar mixture of the alkylthio-thiazine or dihydrothiazine and the haloethylamine hydrohalide in a lower alkanol such as ethanol. The product after isolation may be converted to a pharmaceutically acceptable salt by standard procedures.

An alternative procedure for preparing 2,3-dihydro-7H-imidazo[2,1-b][1,3] thiazine is as follows:

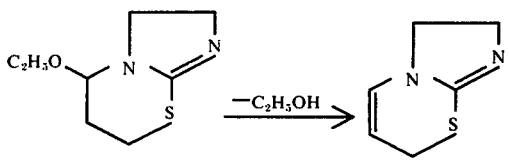

The process comprises heating the 5-ethoxy compound in a high boiling solvent such as toluene in the presence of 4A molecular sieves at 75°–150° C. for 24–72 hours.

The preparation of the novel compounds of this invention and of the necessary starting materials are fully described in the examples that follow.

EXAMPLE 1

2,3-Dihydro-8H-imidazo[2,1-c][1,4]thiazine

Step A:

Preparation of 3,4-dihydro-3-oxo-2H-[1,4]thiazin

A mixture of 25 g. of thioglycolamide, 55 ml. of chloroacetal, 11.5 g. of sodium hydroxide, 1 g. of potassium iodide, and 250 ml. of methanol was refluxed overnight. After cooling, the mixture was adjusted to pH 7 with hydrochloric acid, filtered, and evaporated to dryness. The residue was dissolved in ethanol, filtered and again concentrated to dryness. The oily residue was pyrrolyzed in a distillation apparatus at a bath temperature of 170° C. and about 5 mm. of Hg. of pressure providing 11 g. of a distillate (129°–131° C.), which was chromatographed on silica gel by elution with ethyl acetate:benzene (1:4 v/v) to give 8 g. of pure 3,4-dihydro-3-oxo-2H-[1,4]thiazin, m.p. 65°–68° C.

Step B:

Preparation of 3,4-dihydro-3-thio-2H-[1,4]thiazine

A mixture of 7g of 3,4-dihydro-3-oxo-2H-[1,4]thiazin, 13.5 g. of phosphorus pentasulfide, and 120 g. of pyridine was warmed at 75° C. for 30 minutes, poured into 300 ml. of methylene chloride and stirred for 10 minutes. The solvents were decanted, the residue was extracted twice with hot chloroform, and the extract was concentrated to dryness. The residue was re-extracted with hot 10 × 100 ml. of chloroform, dried, and the combined extracts were concentrated to dryness. The residue was chromatographed on silica gel by elution with chloroform to give 2.4 g. (30%) of pure 3,4-dihydro-3-thio-2H-[1,4]thiazine, m.p. 87-89° C.

Step C:

Preparation of 3-ethylthio-2H-[1,4]thiazine

A mixture of 2 g. of 3,4-dihydro-3-thio-2H-[1,4]thiazine, 2.9 g. of triethyloxonium fluoroborate, and 33 ml. of methylene chloride was stirred for 1.5 hours at ambient temperature. A solution of 7 g. of potassium carbonate in 5 ml. of water was added and stirred vigorously for 10 min. The mixture was filtered, and the organic phase of the filtrate was separated, dried and concentrated to dryness (2.1 g.). The residue was chromatographed on silica gel by elution with benzene to give 1.3 g. (54%) of oily 3-ethylthio-2H-[1,4]thiazine.

Step D:

Preparation of 2,3-dihydro-8H-imidazo[2,1-c][1,4]thiazine

A mixture of 160 mg. 3-ethylthio-2H-[1,4]thiazine, 205 mg. of bromoethylamine hydrobromide, and 3 ml. of ethanol was stirred under nitrogen at room temperature for two hours when one equivalent of potassium carbonate was added. Stirring was continued overnight. The mixture was filtered and concentrated to dryness. The residue was dissolved in 0.5 N hydrochloric acid, and extracted with chloroform. The aqueous phase was made strongly basic with 20% sodium hydroxide solution and extracted 3 times with chloroform, and the extract was concentrated to dryness. The residue was dissolved in 10 ml. of 15% aqueous acetic acid, washed with 5 × 3 ml. of chloroform, basified with 20% sodium hydroxide solution and extracted with 2 × 10 ml. of chloroform. The extract was dried, and concentrated to dryness to give 100 mg. of oil. The oil was dissolved in isopropanol and treated with an equivalent of fumaric acid in methanol. The precipitate was collected and air dried to give 120 mg. of 2,3-dihydro-8H-imidazo[2,1-c][1,3]thiazine fumarate salt, m.p. 163° (dec.).

Employing the procedure of Example 1, Step D, but substituting for the 3-ethylthio-2H-[1,4]thiazine, used therein, an equimolar amount of 3-ethylthio-5-methyl-2H-[1,4]-thiazine, 2-methylthio-4,5-dihydro-6H-[1,3]thiazine, or 2-methylthio-6H-[1,3]thiazine, there is produced respectively., 2,3-dihydro-5-methyl-8H-imidazo[2,1-c][1,4]thiazine fumarate; 2,3,5,6-tetrahydro-7H-imidazo[2,1-b][1,3]thiazine fumarate; or 2,3-dihydro-7H-imidazo[2,1-b][1,3]thiazine fumarate.

EXAMPLE 2

2,3-Dihydro-7H-imidazo[2,1-b][1,3]thiazine

Step A:

Preparation of 5-ethoxy-2,3,5,6-tetrahydro-6H-imidazo[2,1-b][1,3]thiazine

A mixture of 35.7 g. of 2-thioimidazolidine, 87.5 g. of β-chloropropionaldehyde diethyl acetal and 11.62 g. of potassium iodide was refluxed in 1400 ml. of absolute ethanol for 4 days. The mixture was concentrated to dryness. The residue was dissolved in water, extracted with 6 portions of ether, basified with excess sodium hydroxide solution, and filtered. The filter cake was washed with water and chloroform. The filtrate and washings were extracted 8 times with chloroform. The extract was extracted with excess aqueous oxalic acid solution. This extract was basified and extracted with chloroform to give 31.3 g. (48%) of oily 5-ethoxy-2,3,5,6-tetrahydro-6H-imidazo[2,1-b][1,3]-thiazine.

Step B:

Preparation of 2,3-dihydro-7H-imidazo[2,1-b][1,3]-thiazine

A solution of 21.3 g. of 5-ethoxy-2,3,5,6-tetrahydro-6H-imidazo[2,1-b][1,3]thiazine in 1200 ml. of toluene in the presence of 200 g. of molecular sieves 4A was stirred and refluxed for 2 days. The mixture was filtered and concentrated to dryness to give 10.09 g, of crude product. This was dissolved in 250 ml. of absolute ethanol, filtered through diatomaceous earth, and treated with a slight excess oxalic acid. Ether was added to incipient cloudiness and the mixture was cooled. A precipitate of 6.2 g. of 2,3-dihydro-7H-imidazo[2,1-b][1,3]-thiazine oxalic acid salt was obtained which after recrystallization from methanol-ether had m.p. 118° C (slow decomp.).

EXAMPLE 3

Pharmaceutical Compositions

A typical tablet containing 20 mg. of 2,3-dihydro-8H-imidazo[2,1-c][1,4]thiazine fumarate per tablet is prepared by mixing together with the active ingredient calcium phosphate, lactose and starch in the amounts shown in the table below. After these ingredients are thoroughly mixed, the dry mixture is blended for an additional three minutes. This mixture is then compressed into tablets weighing approximately 129 mg. each. Similarly prepared are tablets containing 2,3-dihydro-5-methyl-8H-imidazo[2,1-c][1,4]thiazine fumarate, 2,3,5,6-tetrahydro-7H-imidazo[2,1-b][1,3]thiazine fumarate, or 2,3-dihydro-7H-imidazo[2,1-b][1,2]thiazine fumarate.

| Ingredient | Tablet Formula Mg. per tablet |
|---|---|
| Active Ingredient | 20 mg. |
| Calcium phosphate | 52 mg. |
| Lactose | 45 mg. |
| Starch | 10 mg. |
| Magnesium stearate | 1 mg. |

What is claimed is:
1. A compound of structural formula:

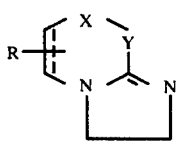

or pharmaceutically acceptable salt thereof, wherein the dotted line represents saturation or unsaturation;
—X—Y—represents—$CH_2$—S or —S—$CH_2$—; and
R represents $C_{1-2}$ alkyl,
with the proviso that if X-Y represents —S—$CH_2$—, the dotted line represents unsaturation.
2. The compound of claim 1 with structural formula:

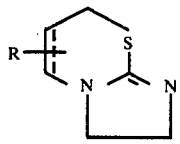

or pharmaceutically acceptable salt thereof.
3. A method of inhibiting indoleamine-N-methyl transferase in a patient in need of such treatment which comprises the administration of an effective amount of a compound of structural formula:

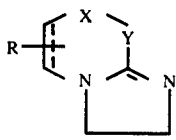

or pharmaceutically acceptable salt thereof, wherein the dotted line represents saturation or unsaturation;
—X—Y— represents —$CH_2$—S— or —S—$CH_2$—; and
R represents $C_{1-2}$ alkyl,
with the proviso that if X—Y represents —S—$CH_2$—, the dotted line represents unsaturation.
4. The method of claim 3, wherein the compound has structural formula:

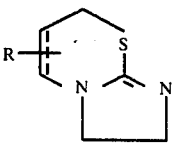

or pharmaceutically acceptable salt thereof.
5. A pharmaceutical composition comprising a pharmaceutical carrier and an effective amount of a compound of structural formula:

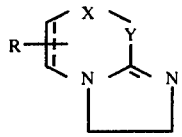

or pharmaceutically acceptable salt thereof, wherein the dotted line represents saturation or unsaturation;
X—Y— represents —$CH_2$—S— or —S—$CH_2$—; and
R represents $C_{1-2}$ alkyl,
with the proviso that if X—Y represents —S—$CH_2$—, the dotted line represents unsaturation.
6. The composition of claim 5, wherein the compound has structural formula:

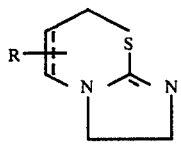

or pharmaceutically acceptable salt thereof.
7. A process for the preparation of a compound of structural formula:

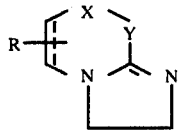

or pharmaceutically acceptable salt thereof, wherein the dotted line represents saturation or unsaturation;
—X—Y— represents —$CH_2$—S— or —S—$CH_2$—; and
R represents $C_{1-2}$ alkyl,
with the proviso that if X—Y represents —S—$CH_2$—, the dotted line represents unsaturation, characterized in that a compound of formula:

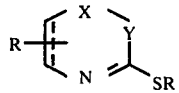

wherein —X—Y—, and R are as defined above, is treated with a compound of formula:

X'($CH_2$)$_2$NH$_2$·NX' wherein X' is chloro or bromo.
8. The process of claim 7 for the preparation of the compound of formula:

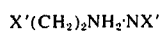

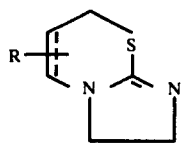
or pharmaceutically acceptable salt thereof.
9. A process for the preparation of a compound of formula:
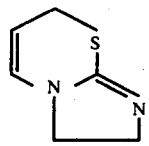
characterized in that a compound of structural formula:
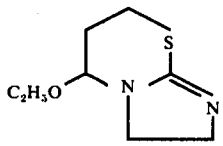
is heated in the presence of 4A molecular sieves.
* * * * *